United States Patent [19]

Van Sin et al.

[11] Patent Number: 5,346,604
[45] Date of Patent: Sep. 13, 1994

[54] SELF-ACTIVATING CHEMICAL SENSOR SYSTEM

[75] Inventors: Kee Van Sin, Lino Lakes; Carter Anderson, Eagan; Kellie Erbisch, Columbia Heights, all of Minn.

[73] Assignee: Diametrics Medical, Inc., Roseville, Minn.

[21] Appl. No.: 964,583

[22] Filed: Oct. 21, 1992

[51] Int. Cl.$^5$ ............................................. G01N 27/404
[52] U.S. Cl. .................................. 204/415; 204/153.17; 204/400
[58] Field of Search ........................... 204/153.17, 415

[56] References Cited

U.S. PATENT DOCUMENTS

| | | | |
|---|---|---|---|
| 3,410,778 | 11/1968 | Krasberg | 204/415 |
| 3,503,861 | 3/1970 | Volpe | 204/415 |
| 3,700,579 | 10/1972 | Clifton et al. | 204/415 |
| 4,734,184 | 3/1988 | Burleigh et al. | 204/415 |
| 4,933,048 | 6/1990 | Lauks | 204/416 |

*Primary Examiner*—T. Tung
*Attorney, Agent, or Firm*—Haugen and Nikolai

[57] ABSTRACT

A gaseous oxygen electrochemical sensing system sustains inter-electrode ionic conductivity by the use of a combination of an hydrophilic coating layer on a gas-permeable barrier or separation membrane to supply sufficient moisture to the electrolyte of an electrode system to activate the sensor and sustain proper operation.

12 Claims, 3 Drawing Sheets

SELF-ACTIVATING CHEMICAL SENSOR SYSTEM

BACKGROUND OF THE INVENTION

I. Field of the Invention

The present invention is directed generally to autogenous packaged, chemical or electrochemical analytical cell systems. More particularly, the invention involves a self-activating chemical sensor for sensing the concentration of gaseous oxygen in an atmosphere. The oxygen sensor includes a self-activating, hydrophilic outer layer which uses the atmosphere humidity to provide sufficient moisture to a hydratable electrolyte to activate and permit stable operation of the oxygen sensor without the need for pre-conditioning.

II. Description of the Related Art

The field of diagnostic medicine is fast becoming more sophisticated and complex. Instrumentation of the class includes devices that monitor and make critical determinations pertaining to ongoing life-threatening conditions. Hence, a great need exists for devices that reduce the time required to make many of these determinations in order that proper, timely corrective steps may be taken to improve or stabilize the condition of the patient, for example, during surgery or during the treatment of traumatic injury. In this regard the analysis of gases including the partial pressures of oxygen ($PO_2$) and carbon dioxide ($PCO_2$) in the blood (blood gas analysis) are examples of extremely important instantaneous indications of respiratory deficiency, efficiency of inhalation therapy, renal function and other vital bodily processes.

Presently, such measurements are made utilizing stationary electrochemical clinical laboratory instruments that have large reference electrodes together with an array of sensors including pH, $CO_2$ and $O_2$ sensors. Periodic recalibration and the running of frequent control samples is required. Calibration and operation measurements using the instrument, to be accurate, are generally restricted to a specific known temperature, e.g., 37° C. The reference and pH electrodes must be calibrated using a liquid media of known composition. The $CO_2$ and $O_2$ electrodes can be calibrated using either liquid medium or a calibration gas, but liquids here also have restrictive temperature ranges for use. This occurs because the composition of typical liquid control or calibration fluid systems is such that the equilibrium partial pressures of oxygen and carbon dioxide are temperature dependent and so reference values occur only at a specific temperature. Exposing the liquid-based calibration system at a temperature other than that designed may introduce a decided amount of error into the readings. Use of calibration gas, of course, requires provision of cylinders of compressed gas of known composition.

It is readily apparent that a portable blood-gas analysis system, particularly one providing a self-calibrating system which is small, easily portable and ambient temperature independent would offer a great advantage. This could eliminate the need for running control samples and would allow calibration to be made at the time of testing. Rapid results would be available to the attending physician at patientside during a procedure.

One alternate prior approach to oxygen calibration using oxygen dissolved in a liquid medium involves the use of relatively inert fluids which have the ability to dissolve rather large amounts of oxygen and which are stable with respect to biological media. One class of such materials consists of certain fluorinated organic compounds known as perfluorocarbons. Perfluorocarbon based systems may provide stable concentrations of oxygen in the calibration medium despite changes in temperature of the calibration medium or solvent within a reasonable range of ambient temperatures. One such system is illustrated and described in copending application No. 07/806,495, now U.S. Pat. No. 5,223,433 assigned to the same assignee as the present invention.

Another prior approach is disclosed respecting an oxygen sensor contained in a bank of electrochemical sensors housed in a disposable cartridge for sensing a plurality of components in which the oxygen sensor is activated by a hydrating liquid just before use. That oxygen sensor employs a layered structure in which two layers are disposed over Ag/AgCl and platinum electrodes. The lower layer next to the electrodes is a layer of a dried residue of a hygroscopic material containing hydratable saccharide or polysaccharide material and an amount of electrolyte salt such as KCl and the upper or outer layer is a water and gas-permeable hydrophobic film formed polymeric layer. The sensor is designed to remain in the dry state until pre-conditioned for first use. Just prior to use, an aqueous liquid calibrating solution is caused to reside above the outer layer and water passes by permeation through the outer layer to hydrate the hygroscopic material and activate the sensor cell. While this system is generally successful, it does have several limiting factors. Those include the pre-conditioning time delay required to allow hydration of the hygroscopic material and activation of the system and the requirement that calibration be made using oxygen dissolved in a liquid medium. Furthermore, the preferred hydrophilic materials are ones tending to swell significantly when hydrated which further tends to slow sensor response.

The present invention, on the other hand, involves a simple, stable and accurate three-layer approach to a sensor for the determination of gaseous or atmospheric oxygen that includes a relatively self-hydrating device. Chemical oxygen detectors or sensors of the type typically used for quantitatively sensing oxygen even in a relatively dry gaseous state require electrolyte medium in conducting state medium connecting the electrodes to activate and operate the sensor. The invention allows the requirement to be met by maintaining sufficient humidity in the atmospheric environment of the oxygen sensor, such that gaseous oxygen sensing is stabilized with respect to the storage, calibration and use of the oxygen sensor without need for pre-conditioning.

Accordingly, it is an object of the present invention to provide an oxygen sensor system which is self-activated from the "dry state" using storage atmospheric humidity which is ready to detect oxygen in a gaseous atmosphere without pre-conditioning.

Another object of the invention is to reduce the response time for an electrochemical oxygen sensor which includes an hydrophilic layer in conjunction with a gas-permeable membrane for gaseous oxygen sensing.

A further object of the invention is to provide an oxygen sensor for a self-contained measurement/calibration cartridge having an autogenous calibration capability for pH, $CO_2$ and $O_2$ in which the $O_2$ is calibrated in the gaseous phase and measured from a blood sample.

A still further object of the invention is the provision of a gaseous oxygen sensing electrode system which will withstand introduction of a liquid blood sample without detrimental effects.

SUMMARY OF THE INVENTION

The present invention provides a miniaturized gaseous oxygen chemical sensor cell capable of in-line disposition with liquid calibrated reference, pH and $CO_2$ electrodes. The oxygen sensor system of the invention includes an electrode system and what initially is a three-layer membrane/electrolyte system. The three-layer system includes an outer composite hydrophilic layer that attracts water vapor combined with a middle gas-permeable polymer membrane barrier layer that transports water vapor molecules to the third layer which is an inner electrolyte layer overlaying the electrode. The sensor is activated or rendered conductive by the water vapor to promote ionic conduction between the electrodes. The system further allows equilibrium diffusion of gaseous oxygen to the electrodes.

The hydrophilic outer layer is one characterized by hygroscopic or hydrophilic material formulated to remove water vapor from the environment and make it available for transport across the inner gas-permeable layer. The preferred hydrophilic material is a mono- or polysaccharide such as sucrose. This is used together with an amount of polyvinyl pyrrolidone and an amount of a preservative such as proclin. Where a plurality of diverse in-line sensors are used in close or contiguous relation to the oxygen sensor, salts common to the calibration media of the other sensors and in like concentrations may also be added to minimize cross-contamination.

The hydrophilic material is designed to remain in place after manufacture, during transport and storage and through calibration of the oxygen sensor but thereafter must be capable of easy removal by the washing action produced by the addition of the liquid sample to be tested after calibration. The hydrophilic outer layer is, in effect, washed off of the semi-rigid gas-permeable membrane and replaced by the sample material. The thickness is typically less than 30 mil.

The gas-permeable semi-rigid membrane may be of polyvinyl chloride (PVC) or other material having the requisite chemical inertness combined with the desired permeability. The thickness of the semi-rigid membrane, depending on composition and density, may be from 0.01 to 3.0 mil. The electrolyte layer contains an electrolyte salt such as potassium chloride (KCl) in a medium such as polyvinyl alcohol (PVA) and is generally less than about 3 mil thick. The electrode system itself preferably consists of thick film, silver and gold electrodes deposited on a dielectric substrate and conventionally connected externally of the cell.

The oxygen sensing system is manufactured in the relatively dry state (no added humidity). It is thereafter preferably packaged and stored until use in an environment containing sufficient available water vapor to activate the sensor. In a multi-sensor cartridge system, the cartridge itself is preferably stored in packaged environment of relatively high humidity and having the oxygen content of air. In this manner, using the system of the present invention, the oxygen sensor is active and at equilibrium with the atmosphere at the time of extraction from the package. This allows instant calibration with no need for a start-up hydration period and using a gaseous environment.

The primary use of the self-activating gaseous oxygen sensing system of the invention is with a self-contained, self-calibrating disposable cartridge for insertable use with an associated diagnostic instrument in which reference, pH, $CO_2$ and possibly $K^+$ and/or other electrolyte ion sensing chemical sensors are combined in an enclosure with the oxygen sensing system in a flow-through analytical cell which further may be a hollow channel. The oxygen sensor is one of an array of in-line chemical sensors in communication with the interior of the flow-through analytical cell which is self-calibrating with respect to its use with the associated diagnostic instrument.

BRIEF DESCRIPTION OF THE DRAWINGS

In the drawings, wherein like numerals are utilized to designate like parts throughout the same.

DETAILED DESCRIPTION

The chemical oxygen sensor of the invention may be suitable for many applications, but in the preferred embodiment is intended as one of a series of in-line sensors contained in a flow through, plug-in cartridge-type diagnostic device. The plug-in cartridge carries the necessary input/output electrical connections and conductors. The cartridge further carries calibration material for several other sensors and a reference electrode. This material is preferably predisposed to dwell at the location of these sensors to also avail them of the ability of instant calibration. For this reason, an amount of at least one viscous calibration material is predisposed and stored in the flow-through analytical cell in contact with the chemical sensors other than the oxygen sensor as required for the calibration of those sensors.

The oxygen sensor, on the other hand, is left exposed to measure the gaseous oxygen of the package environment. The cartridge unit is preferably stored in a controlled environment until opened for use. The atmosphere of the controlled environment is typically one which provides the ability to control the partial pressure of the gas or gases of interest sought to be determined by the several sensors in the flow-through analytical chamber and for which the cell electrodes are to be calibrated. The oxygen composition of the atmosphere of the package is preferably close to that of air in percentage composition to minimize environmental perturbation.

The sensor of the invention has an electrode system in conjunction with a series of over layers. The invention proposes a three-layer storage and calibration configuration and a two-layer measurement configuration. The layers include an outer hydrophilic layer which is one which responds as a humectant to attract environmental water vapor or humidity to provide sufficient conduction at the electrodes to operate the chemical oxygen sensor system and is used in combination with a rigid or semi-rigid, gas-permeable control barrier membrane layer to transport water vapor to an inner electrolyte system and provide an activating amount of ionic conduction at the sensor electrode system. The controlled atmosphere of the package is further provided with sufficient humidity to maintain the operability of the oxygen sensing system throughout storage and calibration as will be discussed in greater detail.

Figure 1:
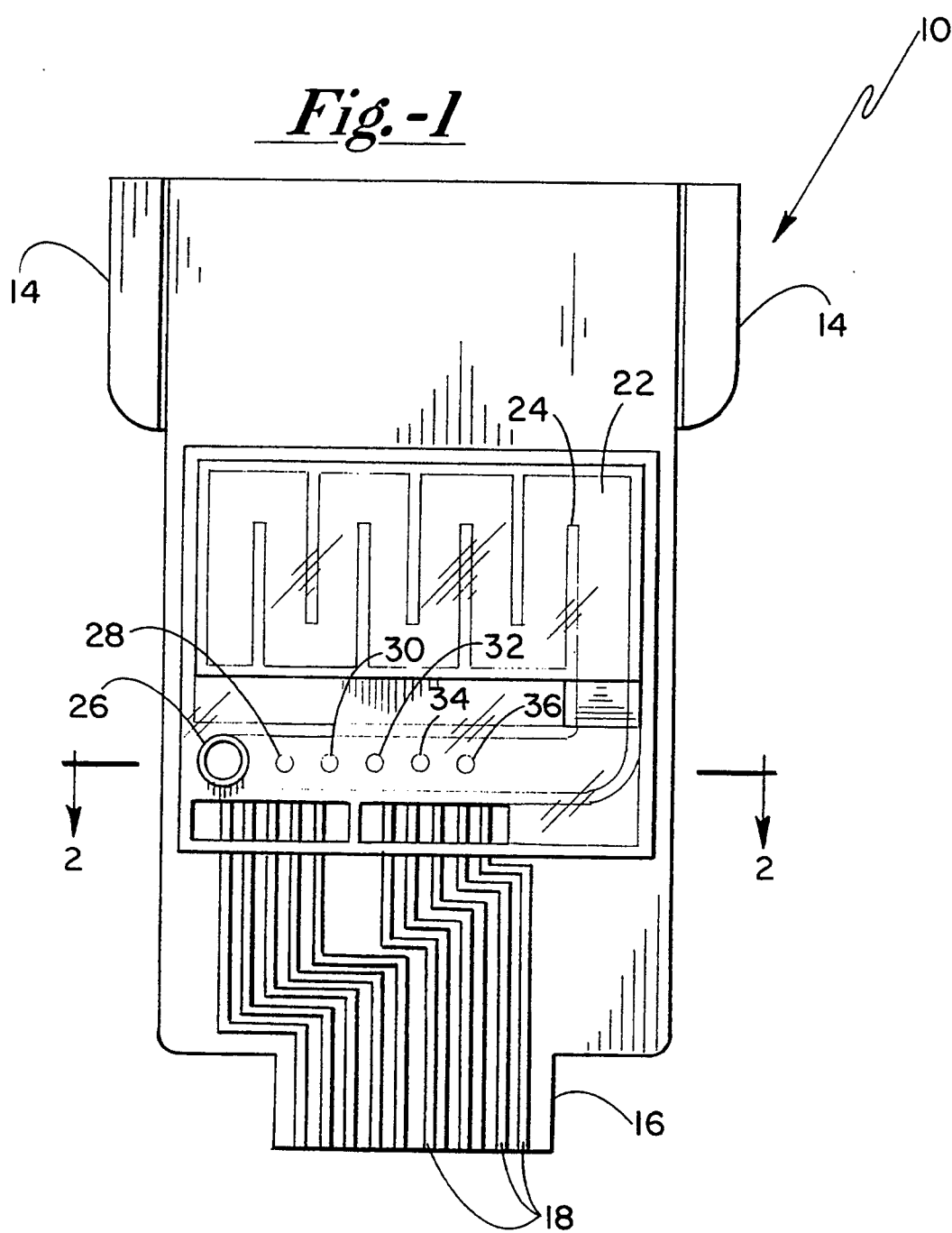
FIG. 1 is a top plan view of a disposable cartridge usable with the oxygen sensor of the present invention.
Figure 2:
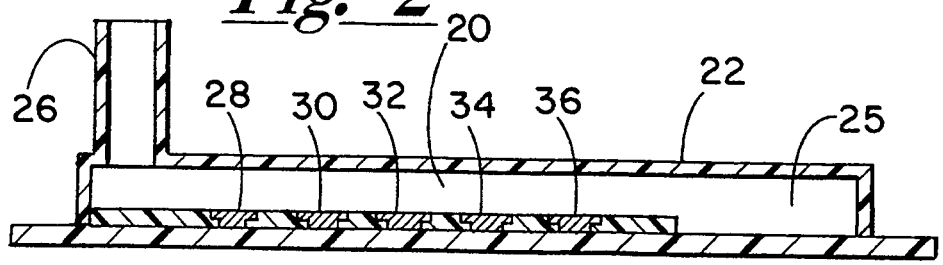
FIG. 2 is a sectional elevational view of the cartridge of FIG. 1 as designed by lines 2—2 in FIG. 1.

With regard to a more specific embodiment, FIG. 1 depicts generally at 10 a disposable cartridge unit designed to be received in a portable diagnostic machine that contains the power supply for and all of the electronics and other associated support equipment required to utilize the cartridge in the manner intended, yet which itself does not form a part of the invention. This, of course, includes means to calibrate all of the electrodes and, upon injection of the sample, make all of the measurement determinations in the sample with respect to that calibration. The cartridge 10 is intended to be employed as a disposable unit for use on a one-time basis for automatic calibration and sample measurement or testing by the associated instrument.

The disposable cartridge 10 includes a shell constructed of a sufficiently rugged polymer material such as polycarbonate and includes an integral flanged handle (not shown) provided to grasp the cartridge and guide members 14 which aid the insertion of end 16 into a corresponding associated portable diagnostic instrument. The cartridge is provided with an array of functional electrical conductors as at 18 which provide the required cartridge/instrument interconnects including all necessary input and output connections. The conductors may be constructed in any well-known manner. They may be deposited on the surface of the polymeric material utilizing thick or thin film technology or any other appropriate technique as may occur to those skilled in the art.

The cartridge unit itself contemplates a plurality of internal passages or chambers including a calibration and measurement flow-through cell chamber 20 and a used calibration medium or excess sample storage chamber 22 which may have a plurality of partitions 24 thereby defining a tortuous maze. The compartment 22 is connected with the electrode-containing measurement compartment 20 via a fluid passage 25. The system also includes a sample inlet port 26 and a plurality of in-line sensor electrodes including a reference electrode 28, pH and $CO_2$ sensors 30 and 32, $K^+$ electrode 34 and the $O_2$ sensor system of the invention is depicted generally at 36. The electrode arrangement in the system, of course, may vary with the desired application.

Figure 3:
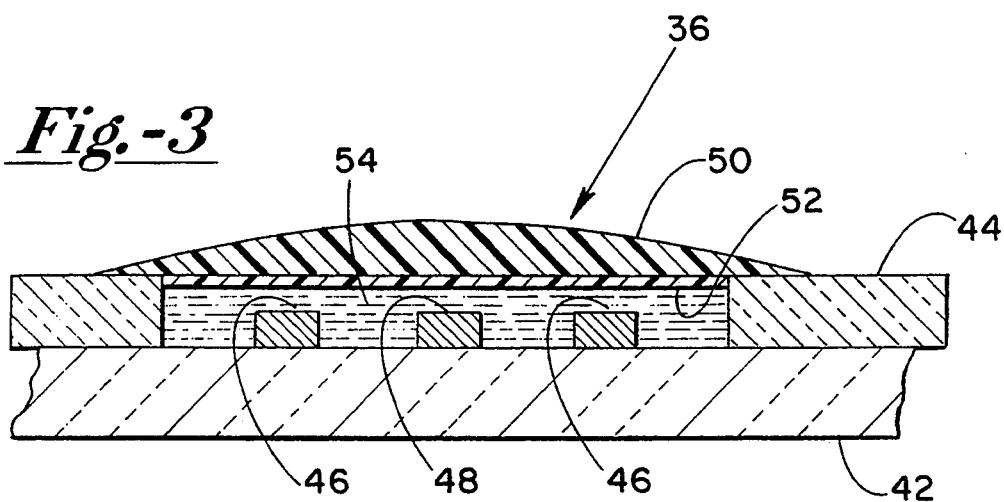
FIG. 3 is a greatly enlarged, broken elevational view of the oxygen sensor system of the invention.
Figure 4:
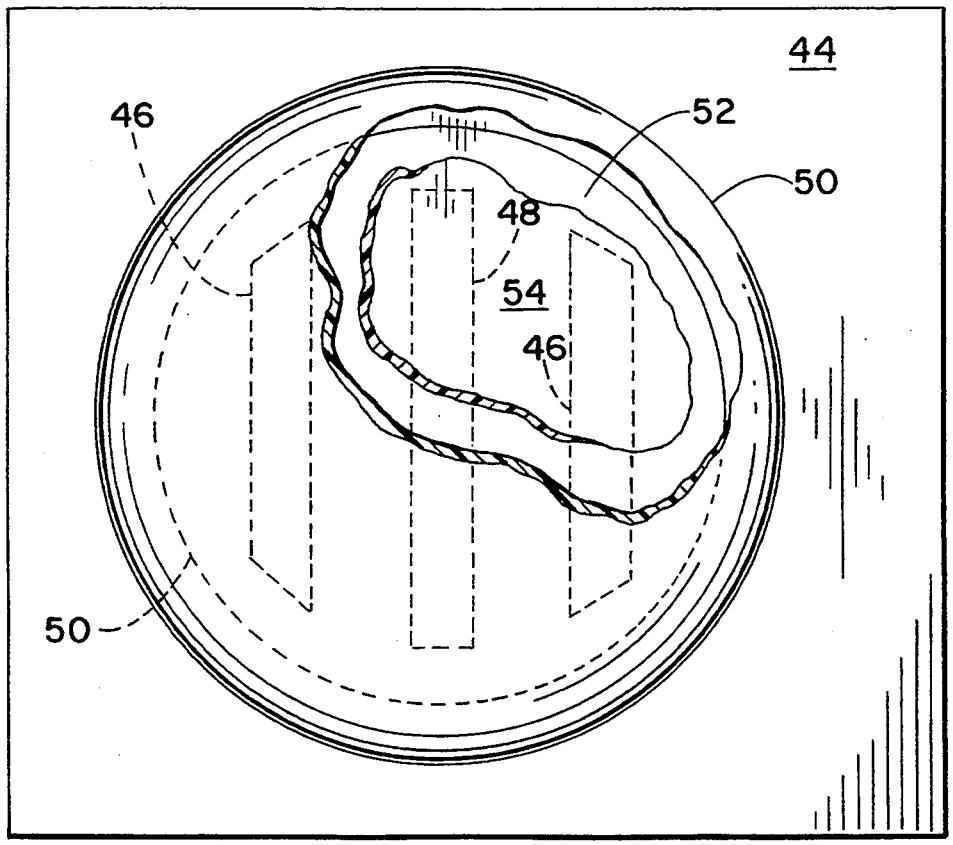
FIG. 4 is a top view of the oxygen sensor of FIG. 3.

FIGS. 3 and 4 depict the oxygen sensor system 36 greatly enlarged and fabricated in accordance with the invention. The sensor system includes a substrate 42, which may be glass or other dielectric ceramic material together with side enclosures as at 44 which also are made of glass or other compatible ceramic or polymeric dielectric material. The sensor has a pair of silver electrodes 46 together with a central gold or other noble metal electrode 48 which may be deposited on the dielectric substrate using any of a plurality of known techniques such as thick film deposition. The electrodes of the oxygen sensor, electrodes 46 and 48, are separated from the environment by a trio of adjacent layers 50, 52 and 54.

The outer layer 50 is an hydrophilic self-activating composite material which, with the oxygen sensor system in the dry state, has the ability to absorb and transmit moisture based on the relative humidity maintained in the cartridge atmosphere, from the cartridge atmosphere to the barrier membrane 52 through which it is, in turn, transmitted in the vapor state into the oxygen sensing system of electrolyte layer 54 such that ionic conduction is maintained between the electrodes 46 and 48 in a manner commensurate with the sensing of the oxygen content in the diffused atmosphere.

The characteristic composition of the outer layer 50 itself is one which combines a hygroscopic or hydrophilic nature, which removes water vapor from the ambient storage atmosphere of the cartridge, absorbing and transmitting it to the membrane 52, which, in turn, transmits water vapor to the electrolyte medium 54. This characteristic is combined with a solubility or removable nature which allows the membrane 50 to be displaced by a liquid sample entering the cartridge through the opening 26, sweeping it into the storage area of the cartridge so that the oxygen content of the sample may thereafter be determined based on oxygen dissolved in the liquid. A preferred embodiment of layer 50 includes a mono- or polysaccharide material, such as sucrose, as the basic hydrophilic material together with an amount of polyvinylpyrrolidone (PVP) and an amount of disinfecting or preservative agent, such as proclin. If desired, amounts of salts utilized in the gel of the calibration material for the reference, pH $CO_2$, $K^+$, etc. may be added to the material making up the membrane 50 such that touching of the membrane material with the gel calibration material for the other sensors will cause no cross-contamination of the calibration material. An amount of deionized water may be used as a vehicle to apply the material to the surface of the membrane 52 during assembly.

Layer 52 may be made, for example, from polyvinyl chloride (PVC), polytetrafluoroethylene (PTFE), polyethylene or any other relatively inert liquid-tight, gas-permeable material. This is intended to be a permanent gas-permeable membrane designed to allow the sensor to reach equilibrium with dissolved gases and a liquid sample quickly or atmospheric oxygen and water vapor with respect to the atmosphere contained in the cartridge 10.

The third or inner layer 54 covers and connects the electrodes 46 and 48 .and fills the space including the electrodes beneath membrane 52 including the electrolyte system activated by water vapor transmitted by the layer 52. Manufactured to a dry state, i.e., with no added humidity, the layer 54 is one which readily hydrates with limited swelling or expansion and which contains the electrolyte salts associated with the sensor. The electrolyte salts are typically alkali metal halides, preferably chlorides such as KCl, and the vehicle or solvent is polyvinyl alcohol. In the dry state, of course, the electrolyte system does not conduct electricity. As explained in greater detail below, however, when the oxygen sensor is contained in a cartridge 10 stored in an environment of sufficient relative humidity, the three-layer system will cooperate to hydrate the layer 54, rendering it conductive and thereby activating the sensor. The sensor thereafter remains stored in an active state ready for instant use.

Figure 5:
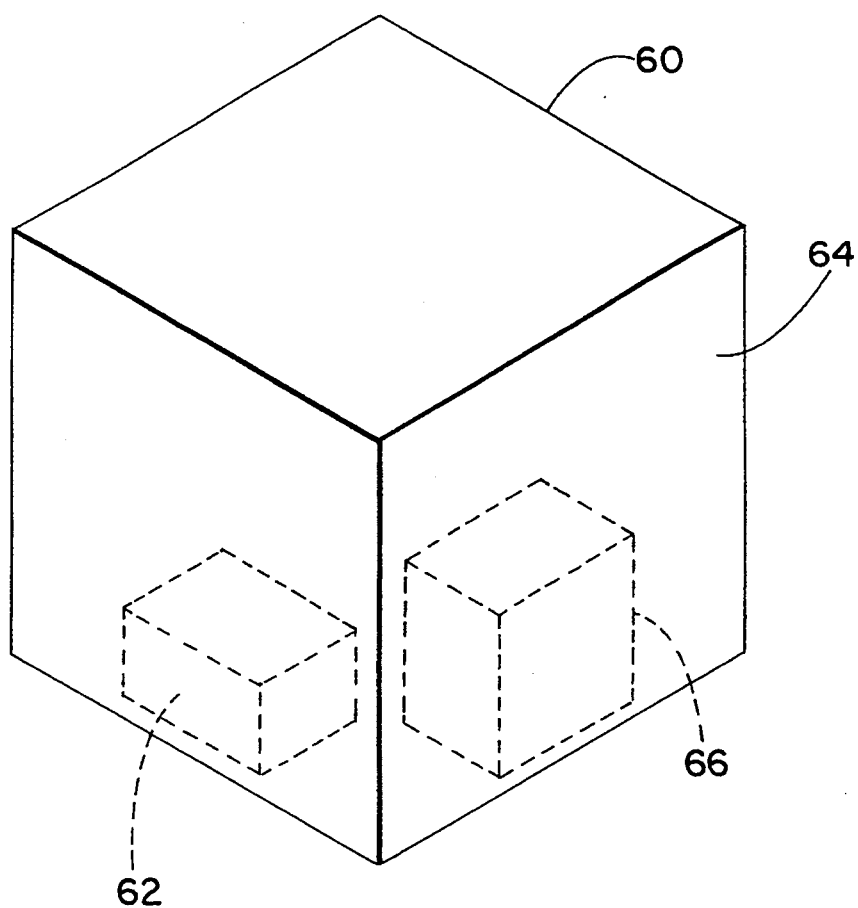
FIG. 5 is a schematic representation of a packaging system in accordance with the storage of the sensor system of the invention.

FIG. 5 depicts a schematic representation of a possible storage construction for the cartridge prior to calibration and use. The environment of the system shown generally in FIG. 4 includes an outer enclosure or package 60 which may be a flexible pouch-type package of poly-foil which has an internal pressure about equal to atmospheric pressure and which is generally impervious to the inward and outward passage of gases and liquids, especially atmospheric molecules including nitrogen, oxygen and carbon dioxide. The package 60 contains the cartridge system represented by 62 which, of course, contains the calibration material, electrodes including the oxygen sensor and is reversibly permeable to the atmosphere contained in the volume 64 in the package 60. The package 60 further contains a reservoir 66 which contains amounts of reversibly absorbable $CO_2$ and, if desired, $O_2$ which buffer the atmosphere in the volume 64 over a range of temperatures such that the percentage of $CO_2$ dissolved in the calibration media together with the amount of $O_2$ in the atmosphere remain substantially constant over a range of ambient temperatures. Such a system is more fully described in co-pending application Ser. No. 07/806,495, filed Dec. 13, 1991 now U.S. Pat. No. 5,223,433 and assigned to the same assignee as the present invention. As required, details from that application needed to complete any understanding of the present application may be deemed incorporated by reference herein.

Briefly, the reservoir 66 is given a higher permeability for the $CO_2$ or other gas of interest than the cartridge 62 so that the relative partial pressure of the species of interest in the space 64 is controlled or dominated by the reservoir 66 rather than the cartridge 62. When package temperature increases and lowers the solubility of the $CO_2$, for example, the reservoir 66 expels $CO_2$ gas into the package atmosphere, raising the pressure of $CO_2$ in the package atmosphere and thereby overcoming the compositional thermodynamic driving force for $CO_2$ to leave the enclosure 62. Conversely, when the system is cooled, the reservoir reverses its action and receives $CO_2$ from the package atmosphere, thereby lowering the partial pressure of the $CO_2$ in the package eliminating any driving force for $CO_2$ in the package atmosphere to dissolve in the sample. So long as the operation of the reservoir system dominates the atmosphere of the cartridge 62, the percentage of dissolved $CO_2$ in the calibration media within the cartridge will remain constant. This can also be done with $O_2$ but is less important if the $O_2$ percentage be maintained at approximately the percentage composition of the normal atmosphere, i.e., about 21%, as this should remain stable with respect to the storage and calibration temperature of the system.

This invention has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications can be accomplished without departing from the scope of the invention itself.

We claim:

1. A self-activating sensing system for detecting oxygen comprising:
   (a) an electrode system including spaced electrodes separated on a dielectric substrate;
   (b) an hydration-activated electrolyte system including a solvent medium containing an electrolyte salt covering and connecting the spaced electrodes;
   (c) a liquid-tight, gas-permeable vapor transport layer physically covering the electrode system and electrolyte system for permitting passage of ambient gases including water vapor to the electrolyte system;
   (d) an outer electrolyte-activating layer on the vapor-transport layer comprising an hydrophilic material for absorbing water vapor from the ambient atmosphere for passage via the vapor transport layer to the electrolyte system to thereby activate the sensing system upon the assembly thereof and maintain the sensing system in an active state during storage, said electrolyte-activating layer further being of a material readily displaced from the vapor transport layer by an aqueous sample; and
   (e) means connecting the electrodes to external circuitry.

2. The sensing system of claim 1 wherein the electrolyte system, vapor transport layer and electrolyte-activating layer consist of three serially abutting layers.

3. The sensing system of claim 2 wherein the total thickness of the electrolyte system, vapor transport layer and electrolyte-activating layer is less than 36 mils.

4. The sensing system of claim 1 wherein the electrolyte-activating layer comprises a material selected from the group consisting of water soluble monosaccharides and polysaccharides and said electrolyte-activating layer further comprises polyvinyl pyrrolidone and optionally an amount of a preservative.

5. The sensing system of claim 4 wherein the electrolyte-activating layer comprises sucrose.

6. The sensing system of claim 5 wherein the electrolyte-activating layer has a thickness less than 30 mils.

7. The sensing system of claim 1 wherein the electrolyte-activating layer is readily removed by a blood sample.

8. The sensing system of claim 1 wherein the vapor transport layer is a material selected from the group consisting of polyvinyl chloride, polytetrafluoroethylene and polyethylene.

9. The sensing system of claim 8 wherein the vapor transport layer is polyvinyl chloride.

10. The sensing system of claim 9 wherein the thickness of the vapor transport layer is from about 0.01 to 3.0 mil.

11. A three-layer, oxygen sensor for detecting oxygen and for storage in the active state comprising:
   (a) an electrochemical system comprising spaced electrodes spanned by a layer of hydration-activated electrolyte medium;
   (b) a liquid-tight, gas permeable vapor transport layer on the electrolyte layer for transporting gases including water vapor to the electrolyte layer; and
   (c) an outer layer of hydrophilic material on the vapor transport layer for absorbing water vapor from the ambient atmosphere for passage via the vapor transport layer to the electrolyte to thereby activate the electrochemical system and maintaining same in an active state prior to calibration and use, said hydrophilic material further being one readily displaced from the vapor transport layer by an aqueous sample.

12. A self-activating electrochemical quantitative oxygen measuring system for determining the oxygen content of a gaseous sample designed to be stored in the active state comprising:
   (a) spaced electrodes carried on a dielectric substrate;
   (b) a hydratable, hydration-activated electrolyte layer on an connecting the electrodes;

(c) a gas-permeable, liquid impervious vapor transport membrane overlaying the electrodes and electrolyte layer;

(d) an outer layer of water soluble hydrophilic material on the vapor transport membrane, wherein the outer layer coats the vapor transport membrane but readily disperses when contacted with water based samples;

(e) wherein the outer layer and the gas-permeable vapor transport membrane cooperate to provide sufficient water vapor to the electrolyte to activate the electrode system upon assembly and thereby maintain the electrolyte conduction between the electrodes during a shelf life of the system.

* * * * *